United States Patent [19]

Sandell

[11] Patent Number: 5,474,971
[45] Date of Patent: Dec. 12, 1995

[54] WATER-DISPERSIBLE GRANULAR AGRICULTURAL COMPOSITIONS MADE BY HEAT EXTRUSION

[75] Inventor: Lionel S. Sandell, Wilmington, Del.

[73] Assignee: E. I. Du Pont de Nemours and Company, Wilmington, Del.

[21] Appl. No.: 107,780

[22] PCT Filed: Feb. 27, 1992

[86] PCT No.: PCT/US92/01262

§ 371 Date: Aug. 26, 1993

§ 102(e) Date: Aug. 26, 1993

[87] PCT Pub. No.: WO92/15197

PCT Pub. Date: Sep. 17, 1992

Related U.S. Application Data

[63] Continuation of Ser. No. 662,698, Mar. 1, 1991, abandoned.

[51] Int. Cl.⁶ .......................... A01N 25/08; A01N 25/12; A01N 47/36
[52] U.S. Cl. .......................... 504/116; 504/212; 504/213; 504/214; 504/215; 504/330; 424/409; 71/DIG. 1
[58] Field of Search ...................................... 504/116, 212, 504/213, 214, 215, 330; 71/DIG. 1; 424/409

[56] References Cited

U.S. PATENT DOCUMENTS

| | | | |
|---|---|---|---|
| 4,065,289 | 12/1977 | Judd | 71/82 |
| 4,698,264 | 10/1987 | Steinke | 428/402.2 |
| 4,816,298 | 3/1989 | Alderman et al. | 427/212 |
| 4,979,979 | 12/1990 | McCollum, III et al. | 71/93 |
| 5,180,587 | 1/1993 | Moore | 424/408 |
| 5,208,030 | 5/1993 | Hoy et al. | 424/409 |

FOREIGN PATENT DOCUMENTS

| | | |
|---|---|---|
| 890398 | 1/1972 | Canada . |
| 080862 | 6/1983 | European Pat. Off. . |
| 0206537 | 12/1986 | European Pat. Off. . |
| 0256608 | 2/1988 | European Pat. Off. . |
| 47-23199 | 6/1972 | Japan . |
| 52-030577 | 8/1977 | Japan . |
| 54/107521 | 6/1983 | Japan . |
| 2230954 | 11/1990 | United Kingdom . |
| 89-00079 | 1/1989 | WIPO . |
| 91/13546 | 9/1991 | WIPO . |
| 91-13546 | 9/1991 | WIPO . |

*Primary Examiner*—S. Mark Clardy

[57] ABSTRACT

Rapidly disintegrating water-soluble or water-dispersible granular compositions are made by extruding a premix through a die or screen at elevated temperature. The extruded composition is chopped or milled to form a granular product. The compositions contain one or more water-soluble ingredients which soften or melt at elevated temperatures. No water is added in the process thereby eliminating the need for drying.

10 Claims, No Drawings

WATER-DISPERSIBLE GRANULAR AGRICULTURAL COMPOSITIONS MADE BY HEAT EXTRUSION

This application has been filed under 35 USC 371 as a national phase application of PCT/US92/01262, filed Feb. 27, 1992, which was a continuation of Ser. No. 07/662,698, filed Mar. 1, 1991, now abandoned.

BACKGROUND OF THE INVENTION

The present invention relates to water-dispersible granular compositions comprising active ingredients of value in agriculture.

It is advantageous to formulate active pesticides as water-dispersible compositions which can be readily mixed with water and applied by means of a spraying apparatus to a locus to be protected. It is also advantageous that such granular compositions can be readily dispersed or dissolved in water. It is also advantageous that the granular compositions have good attrition resistance, uniform size granules and uniform bulk density.

World Patent WO 89/00079 discloses an extrusion process to make water-dispersible granules of agricultural chemicals in which water is added to make an extrudable wet mix. The extrudate is rolled to break the product down to granules and then optionally dried.

U.S. Pat. No. 4,065,289 discloses a herbicidal composition containing a plant fertilizer component and a herbicide component which is extruded through a die at 70° C.–145° C. The herbicide component acts as a lubricant to permit ready extrusion and to form a coherent extrudate.

SUMMARY OF THE INVENTION

The present invention is directed to rapidly disintegrating water-dispersible granular agricultural compositions comprising by weight based on the total weight of the composition:

1) 0.01–90% of one or more active ingredients;
2) 1–60% of one or more water-soluble diluents;
3) 0–30% of one or more water-soluble heat activated binders that melt at temperatures between 40°–120° C.; and
4) two or more additives selected from the group consisting of:
   a) 0–10% anticaking agent(s);
   b) 0–10% chemical stabilizer(s);
   c) 0–20% gas generating agents;
   d) 0.1–10% wicking or swelling disintegrant(s);
   e) 0.1–20% dispersant(s);
   f) 0–5% wetting agent(s); and
   g) 0–80% inert filler(s).

The sum of all ingredients in a composition is 100%.

The invention is also directed to a process for preparing the compositions of the invention, said process comprising extruding a premix through a die or screen at elevated temperature without using any water. Accordingly, the process of the invention comprises extruding a dry premix comprising by weight based on the total weight of the composition:

1) 0.01–90% of one or more active ingredients;
2) 1–60% of one or more water-soluble diluents;
3) 0–30% of one or more water-soluble heat activated binders that melt at temperatures between 40°–120° C.; and
4) two or more additives selected from the group consisting of:
   (a) 0–10% anticaking agent (s);
   (b) 0–10% chemical stabilizer (s);
   (c) 0–20% gas generating agents;
   (d) 0.1–10% wicking or swelling disintegrant (s);
   (e) 0.1–20% dispersant (s);
   (f) 0–5% wetting agent (s); and
   (g) 0–80% inert filler(s);

through a die or screen at a temperature from 50° C. to 130° C. and chopping or milling the extruded material to form uniform granules.

The active ingredient is at least one chemical used for crop protection or plant growth regulation or pesticide. More specifically, ingredients are selected from the class of herbicides, fungicides, bactericides, insecticides, insect antifeedants, acaricides, miticides, nematocides, and plant growth regulants.

The preferred compositions of the invention are:

1. The composition of the general formula wherein the active ingredient(s) comprise 0.03–80%, the heat activated binder(s) comprise 1–15% and the water-soluble diluent(s) comprise 1–40% by weight based on the total weight of the composition.
2. The composition of Preferred 1 wherein the active ingredient(s) comprise 10–70% by weight.
3. The composition of Preferred 2 wherein the water soluble diluent is urea, ethylurea, sorbitol, lactose or sodium acetate trihydrate and mixtures of the foregoing.
4. The composition of Preferred 3 wherein the heat activated binder(s) is selected from the classes consisting of polyethoxylated alkylphenols and ethylene oxide/propylene oxide copolymers and mixtures of the foregoing.
5. The composition of Preferred 4 wherein the disintegrant(s) is cross-linked polyvinyl pyrrolidone or cross-linked sodium carboxymethyl cellulose.
6. The composition of Preferred 5 wherein the dispersant is a napthalene-sulfonate-formaldehyde condensate or a ligninsulfonate.
7. The composition of Preferred 4 wherein the heat activated binder(s) is a block copolymer of ethylene oxide/propylene oxide where 80% is ethylene oxide and 20% is propylene oxide, or polyethoxylated dinonylphenol with 150 ethylene oxide units.
8. The composition of Preferred 3 wherein the water soluble diluent is urea or sorbitol.
9. The composition of Preferred 8 wherein the active ingredient is N'(3,4-dichlorophenyl)-N,N-dimethyl urea (diuron).
10. The composition of Preferred 8 wherein the active ingredient is methyl 2-benzimidazole-carbamate (carbendazim).
11. The composition of Preferred 8 wherein the active ingredient is 3-cyclohexyl-6-dimethylamino-1-methyl-1,3,5-triazin-2,4-(1H,3H)dione (hexazinone).
12. The composition of Preferred 8 wherein the active ingredient is selected from:
    methyl 2-[[[[(4,6-dimethyl-2-pyrimidinyl)amino]carbonyl]amino]sulfonyl]benzoate;
    methyl 3-[[[[(4-methoxy-6-methyl-1,3,5-triazin-2-yl)amino]carbonyl]amino] sulfonyl] -2-thiophenecarboxylate;

2-chloro-N-[[(4-methoxy-6-methyl-1,3,5 -triazin-2-yl)amino]carbonyl]-benzene-sulfonamide;

ethyl 2-[[[[(4-chloro-6-methoxy-2 -pyrimidinyl)amino] carbonyl]amino] sulfonyl]benzoate;

methyl 2-[[[[(4-methyl-6-methoxy-1,3,5 -triazin-2-yl)amino]carbonyl]amino] sulfonyl] benzoate;

2-[[[[(4,6-dimethoxy-2-pyrimidinyl)amino] carbonyl] amino]sulfonyl]-N, N-dimethyl- 3-pyridinecarboxamide;

methyl 2-[[[[[4-ethoxy-6-(methylamino- 1,3,5-triazin-2-yl]amino]carbonyl] amino]sulfonyl]benzoate;

methyl 2-[[[[N-(4-methoxy-6-methyl-1,3,5 -triazin-2-yl)-N-methylamino]carbonyl] amino]sulfonyl]benzoate;

methyl 2-[[[[[(4,6-dimethoxy-2-pyrimidinyl)amino] carbonyl]amino]sulfonyl] methyl]benzoate;

N-[[(4,6-dimethoxy-2-pyrimidinyl)amino] carbonyl]-3-(ethylsulfonyl)-2-pyridine sulfonamide;

methyl 2-[[[[4,6-bis(difluoromethoxy)-2-pyrimidinyl] amino]carbonyl] amino]sulfonyl]benzoate;

2-(2-chloroethoxy)-N-[(4-methoxy-6 -methyl-1,3,5-triazin-2-yl)aminocarbonyl] benzene sulfonamide;

ethyl 5-[[[(4,6-dimethoxy-2-pyrimidinyl)-amino]carbonyl]amino]sulfonyl] -1-methyl-1H-pyrazole-4-carboxylate; or N-[[(4,6-dimethoxy-2-pyrimidinyl) amino] carbonyl]-1-methyl-4-(2-methyl-2H-tetrazol- 5-yl)-1H-pyrazole-5-sulfonamide.

DETAILED DESCRIPTION OF THE INVENTION

Compositions for agricultural or pesticidal use are usually manufactured and sold as liquid or solid concentrates. In recent years fromulations based on water-dispersible granules have become increasingly popular because they offer several advantages over other types of agricultural formulations. For example, they are stable during storage and transport. Often this is a concern with aqueous suspension concentrates that can settle or develop crystals in storage if the active ingredient has sufficient water solubility. Also, aqueous suspension concentrates are not suitable for active ingredients which are subject to aqueous hydrolysis. This is not a problem with water-dispersible granules. In comparison to wettable powders, water-dispersible granules are convenient to handle and measure and are relatively dust-free. They avoid the skin-toxicity and odor problems associated with solvent-based formualtions such as emulsion concentrates and organic suspension concentrates.

To make water-dispersible granules useful for application they are usually diluted in a mix tank containing water to form a solution or dispersion which can be sprayed. The dispersed particles formed on dilution should be no larger than 50 microns in their largest dimension to avoid nozzle pluggage or premature settling which results in uneven application of the pesticide. It is therefore necessary that all of the components of the formulated product rapidly and completely disperse or dissolve in the dilution water.

Conventional methods for preparing water-dispersible granule compositions involve (1) water-spraying in fluidized bed or pan granulation equipment (2) spray-drying (3) dry compaction and (4) extrusion of a water-wet paste. Granules prepared by fluid-bed, spray-drying or pan granulation can be formulated to disperse rapidly when diluted in water. However these processes require specialized technology including extensive dust collection systems and a space-consuming and expensive drying operation. Dry compaction and extrusion generally do not produce fast-dispersing granules, and wet-extrusion also requires a drying step.

The present invention comprises water-dispersible granular compositions which are made by extruding a dry premix through a die or screen at elevated temperature and chopping or grinding the extruded material to form granules. Advantages of these heat extruded granular compositions include (1) rapid disintegration and good dispersion properties in water (2) good attrition resistance (3) more uniform size and bulk density than granules prepared by fluid-bed or pan granulation, or by other tumbling/mixing processes such as in a rotating drum granulator (4) a simple process which uses readily available commercial extruding equipment, and (5) no need for drying or dust collection equipment.

The compositions of this invention are prepared as follows. An extrudable premix is prepared by combining the pesticidal particles with one or more water-soluble diluents, and preferably one or more water-soluble heat activated binders which soften or melt in the desired temperature range. Other additives included in the premix are wicking or swelling disintegrants and one or more dispersants. Particulate additives such as wetting agents, gas-generating agents, anticaking agents, chemical stabilizers, and inert fillers may optionally be added.

The process of the invention comprises extruding a dry premix comprising by weight based on the total weight of the composition:

1) 0.01–90% of one or more active ingredients;

2) 1–60% of one or more water-soluble diluents;

3) 0–30% of one or more water-soluble heat activated binders that melt at temperatures between 40°–120° C.; and 4) two or more additives selected from the group consisting of:
   a) 0–10% anticaking agent(s);
   b) 0–10% chemical stabilizer(s);
   c) 0–20% gas generating agents;
   d) 0.1–10% wicking or swelliling disintegrant(s);
   e) 0.1–20% dispersant(s);
   f) 0–5% wetting agent(s); and
   g) 0–80% inert filler(s);

through a die or screen at a temperature from 50° C. to 130° C. and chopping or milling the extruded material to form uniform granules.

The preferred embodiments of the process of the invention include the preferred conditions for the compositions recited above and a temperature of from 75° C. to 115° C.

The premix is blended and milled to an average particle diameter between 1 and 50 microns. Preferably, the premix is fed or metered to an extruder that has been heated electrically, by steam, or by other conventional means of heating. Suitable extruders include axial and radial designs with single or twin screws, and roll-type extrusion presses. In some types of extrusion equipment, for example, a California Pellet Mill, the heat can be generated from friction. Other means of heating the premix could include preheating the premix before extrusion, or heating the individual components of the premix before blending. The premix is heated to or maintained at a temperature in the range of about 50° C. to 130° C., preferably about 75° C. to 115° C. The optimum temperature will vary with the composition, but can be determined empirically.

The heated premix is extruded through a die or screen. The die holes range in diameter from 0.25 mm to 7 mm, preferably from 0.4 mm to 2 mm. Depending on the composition and the type of extruder used, the extruded material might be recycled until the strands are uniform in texture. Generally the extruded material is allowed to cool to harden and reduce stickiness, although this may not be necessary. The strands are chopped, milled or rolled and then screened to approximately 10 to 60 U.S. mesh size granules. A narrower cut size range may be selected. In some cases the strands may be sufficiently brittle so that they break on their own into short lengths.

The active ingredient should be chemically stable in the extrusion temperature range. Examples of suitable active ingredients are listed in Table 1.

TABLE 1

| Cmpd. No. | Common Name | m.p. (°C.) | Chemical Name |
|---|---|---|---|
| | | HERBICIDES | |
| 1 | acifluorfen | 142–160 | 5-[2-chloro-4-(trifluoro methyl)phenoxy]-2-nitro-benzoic acid |
| 2 | asulam | 142–144 | methyl [(4-aminophenyl)-sulfonyl]carbamate |
| 3 | atrazine | 175–177 | 6-chloro-N-ethyl-N'-(1-methylethyl)-1,3,5-triazine-2,4-diamine |
| 4 | bensulfuron methyl | 185–188 | 2-[[[[(4,6-dimethoxy-2-pyrimidinyl)amino]-carbonyl]amino]sulfonyl]-methyl]benzoic acid, methyl ester |
| 5 | bentazon | 137–139 | 3-(1-methylethyl)-(1H)-2,1,3-benzothiadiazin-4 (3H)-one, 2,2-dioxide |
| 6 | bromacil | 158–159 | 5-bromo-6-methyl-3-(1-methylpropyl)-2,4(1H,3H) pyrimidinedione |
| 7 | bromoxynil | 194–195 | 3,5-dibromo-4-hydroxy-benzonitrile |
| 8 | chloramben | 200–201 | 3-amino-2,5-dichloro-benzoic acid |
| 9 | chlorimuron ethyl | >100 | 2-[[[[(4-chloro-6-methoxy-2-pyrimidinyl)amino] carbonyl]-amino]sulfonyl] benzoic acid, ethyl ester |
| 10 | chloroxuron | 151–152 | N'-[4-(4-chlorophenoxy)-phenyl]N,N-dimethylurea |
| 11 | chlorsulfuron | 174–178 | 2-chloro-N-[[(4-methoxy-6-methyl-1,3,5-triazin-2-yl)-amino]carbonyl]benzene-sulfonamide |
| 12 | chlortoluron | 147–148 | N'-(3-chloro-4-methylphenyl)-N,N-dimethylurea |
| 13 | clomazone | oil | 2-[(2-chlorophenyl)methyl]-4,4-dimethyl-3-isoxazoli-dinone |
| 14 | cyanazine | 166–167 | 2-[[4-chloro-6-(ethylamino)-1,3,5-triazin-2-yl]amino]-2-methylpropanenitrile |
| 15 | dazomet | 104–105 | tetrahydro-3,5-dimethyl-2H-1,3,5-thiadiazine-2-thione |
| 16 | desmediphan | 120 | ethyl [3-[[(phenylamino)-carbonyl]oxy]phenyl]-carbamate |
| 17 | dicamba | 114–116 | 3,6-dichloro-2-methoxybenzoic acid |
| 18 | dichlobenil | 139–145 | 2,6-dichlorobenzonitrile |
| 19 | dichlorprop | 117–118 | (±)-2-(2,4-dichlorophenoxy)-propanoic acid |
| 20 | diphenamid | 134–135 | N,N-dimethyl-α-phenylbenzene-acetamide |
| 21 | dipropetryn | 104–106 | 6-(ethylthio)-N,N'-bis(1-methylethyl)-1,3,5-triazine-2,4-diamine |
| 22 | diuron | 158–159 | N'-(3,4-dichlorophenyl)-N,N-dimethylurea |
| 23 | thiameturon | >100 | 3-[[[[(4-methoxy-6-methyl-1,3,5-triazin-2-yl)amino]-carbonyl]amino]sulfonyl]-2-thiophenecarboxylic acid, methyl ester |
| 24 | — | >100 | 2-[[[N-(4-methoxy-6-methyl-1,3,5-triazine-2-yl)-N-methylamino]carbonyl]- |

TABLE 1-continued

| Cmpd. No. | Common Name | m.p. (°C.) | Chemical Name |
|---|---|---|---|
| | | | amino]sulfonyl]benzoic acid, methyl ester |
| 25 | fenac | 156 | 2,3,6-trichlorobenzeneacetic acid |
| 26 | fenuron | 133–134 | N,N-dimethyl-N'-phenylurea |
| 27 | fluometuron | 163–164 | N,N-dimethyl-N'-[3-(trifluoromethyl)phenyl]urea |
| 28 | fluridone | 151–154 | 1-methyl-3-phenyl-5-[3-(trifluoromethyl)phenyl]-4(1H)-pyridinone |
| 29 | fomesafen | 220–221 | 5-[2-chloro-4-(trifluoromethyl)phenoxy]-N-(methylsulfonyl)-2-nitrobenzamide |
| 30 | glyphosate | 200. | N-(phosphonomethyl)glycine |
| 31 | hexazinone | 115–117 | 3-cyclohexyl-6-(dimethylamino)-1-methyl-1,3,5-triazine-2,4(1H,3H)-dione |
| 32 | imazamethabenz | >100 | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| 33 | imazaquin | 219–222 | 2-[4,5-dihydro-4-methyl-4-(1-methylethyl)-5-oxo-1H-imidazol-2-yl]-3-quinolinecarboxylic acid |
| 34 | imazethapyr | 172–175 | (±)-2-[4,5-dihydro-4-methyl-4-(1-methylethyl)-5-oxo-1H-imidazol-2-yl]-5-ethyl-3-pyridinecarboxylic acid |
| 35 | ioxynil | 209 | 4-hydroxy-3,5-diiodobenzonitrile |
| 36 | isoproturon | 155–156 | N-(4-isopropylphenyl)-N',N'-dimethylurea |
| 37 | isouron | 119–120 | N'-[5-(1,1-dimethylethyl)-3-isoxazolyl]-N,N-dimethylurea |
| 38 | isoxaben | 176–179 | N-[3-(1-ethyl-1-methylpropyl)-5-isoxazolyl]-2,6-dimethoxybenzamide |
| 39 | karbutilate | 176–178 | 3-[[(dimethylamino)carbonyl]amino]phenyl-(1,1-dimethylethyl)carbamate |
| 40 | lenacil | 316–317 | 3-cyclohexyl-6,7-dihydro-1H-cyclopentapyrimidine-2,4-(3H,5H)dione |
| 41 | MCPA | 100–115 | (4-chloro-2-methylphenoxy)-acetic acid |
| 42 | MCPB | 100 | 4-(4-chloro-2-methylphenoxy)-butanoic acid |
| 43 | mefluidide | 183–185 | N-[2,4-dimethyl-5-[[(trifluoromethyl)sulfonyl]-amino]phenyl]acetamide |
| 44 | methabenzthiazuron | 119–120 | 1,3-dimethyl-3-(2-benzothiazolyl)urea |
| 45 | methazole | 123–124 | 2-(3,4-dichlorophenyl)-4-methyl-1,2,4-oxadiazolidine-3,5-dione |
| 46 | metribuzin | 125–126 | 4-amino-6-(1,1-dimethylethyl)-3-(methylthio)-1,2,4-triazin-5(4H)-one |
| 47 | metsulfuron methyl | 163–166 | 2-[[[[(4-methoxy-6-methyl-1,3,5-triazin-2-yl)amino]carbonyl]amino]sulfonyl]-benzoic acid, methyl ester |
| 48 | monuron | 174–175 | N'-(4-chlorophenyl)-N,N-dimethylurea |
| 49 | naptalam | 185 | 2-[(1-naphthalenylamino)-carbonyl]benzoic acid |
| 50 | neburon | 102–103 | 1-butyl-3-(3,4-dichlorophenyl)-1-methylurea |
| 51 | nitralin | 151–152 | 4-(methylsulfonyl)-2,6-dinitro-N,N-dipropylaniline |
| 52 | norflurazon | 174–180 | 4-chloro-5-(methylamino)-2-[3-(trifluoromethyl)phenyl]- |

TABLE 1-continued

| Cmpd. No. | Common Name | m.p. (°C.) | Chemical Name |
|---|---|---|---|
| | | | 3(2H)-pyridazinone |
| 53 | oryzalin | 141–142 | 4-(dipropylamino)-3,5-dinitro-benzenesulfonamide |
| 54 | perfluidone | 142–144 | 1,1,1-trifluoro-N-[2-methyl-4-(phenylsulfonyl)phenyl]-methanesulfonamide |
| 55 | phenmedipham | 143–144 | 3-[(methoxycarbonyl)amino]-phenyl (3-methylphenyl)-carbamate |
| 56 | picloram | >215 (DEC) | 4-amino-3,5,6-trichloro-2-pyridinecarboxylic acid |
| 57 | prometryn | 118–120 | N,N'-bis(1-methylethyl)-6-(methylthio)-1,3,5-triazine-2,4-diamine |
| 58 | pronamide | 155–156 | 3,5-dichloro-N-(1,1-dimethyl-2-propynyl)benzamide |
| 59 | propazine | 212–214 | 6-chloro-N,N'-bis(1-methyl-ethyl)-1,3,5-triazine-2,4-diamine |
| 60 | pyrazon | 205–206 | 5-amino-4-chloro-2-phenyl-3(2H)pyridazinone |
| 61 | siduron | 133–138 | N-(2-methylcyclohexyl)-N'-phenylurea |
| 62 | simazine | 225–227 | 6-chloro-N,N'-diethyl-1,3,5-triazine-2,4-diamine |
| 63 | sulfometuron methyl | 182–189 | 2-[[[[(4,6-dimethyl-2-pyrimidinyl)amino]carbonyl]-amino]sulfonyl]benzoic acid, methyl ester |
| 64 | tebuthiuron | 161–164 | N-[5-(1,1-dimethylethyl)-1,3,4-thiadiazol-2-yl]-N,N'-dimethylurea |
| 65 | terbacil | 175–177 | 5-chloro-3-(1,1-dimethyl-ethyl)-6-methyl-2,4(1H,3H)-pyrimidinedione |
| 66 | torbuthyl-azine | 177–179 | 2-(tert-butylamino)-4-chloro-6-(ethyl-amino)-_s-triazine |
| 67 | terbutryn | 104–105 | N-(1,1-dimethylethyl)-N'-ethyl-6-(methylthio)-1,3,5-triazine-2,4-diamine |
| 68 | triclopyr | 148–150 | [(3,5,6-trichloro-2-pyri-dinyl)oxy]acetic acid |
| 69 | 2,4-D | 140 | (2,4-dichlorophenoxy)acetic acid |
| 70 | 2,4-DB | 119–120 | 4-(2,4-dichlorophenoxy)-butanoic acid |
| 71 | triasulfuron | >100 | (3-(6-methoxy-4-methyl-1,3,5-triazin-2-yl)-1-[2-(2-chloroethoxy)phenylsulfonyl] urea |
| 72 | primisulfuron | >100 | [2-/3-(4,6-bis(difluoro-methoxypyrimidin-2-yl-ureidosulfonyl)benzoic acid methylester] |
| 73 | — | >100 | [2-/3-(4,6-bis(difluoro-methoxy)-pyrimidin-2-yl)-ureidosulfonyl)-benzoic acid methylester) |
| 74 | NC-311 | 170–172 | [5-pyrazolesulfonamide, N-[(4-methoxy-6-methyl-pyrimidine-2-yl)-amino-carbonyl]-4-methoxy-carbonyl-1-methyl-] |
| 75 | — | 160–162 | N-[[(4,6-dimethoxy-2-pyrimidinyl)amino]carbonyl]-3-(ethylsulfonyl)-2-pyridinesulfonamide |
| 76 | — | 152–159 | 2-[[[[(4,6-dimethoxy-2-pyrimidinyl)amino]carbonyl]-amino]sulfonyl]-N,N-dimethyl-3-pyridine-carboxamide |
| 77 | — | 204–206 | Methyl 2-[[[[(4-ethoxy-6-(methylamino)-1,3,5-triazin-2-yl]amino]carbonyl]amino]-sulfonyl]benzoate |

TABLE 1-continued

| Cmpd. No. | Common Name | m.p. (°C.) | Chemical Name |
|---|---|---|---|
| | | FUNGICIDES | |
| 78 | carbendazim | 302–307 | methyl 2-benzimidazole-carbamate |
| 79 | thiuram | 146 | tetramethylthiuram disulfide |
| 80 | dodine | 136 | n-dodecylguanidine acetate |
| 81 | chloroneb | 133–135 | 1,4-dichloro-2,5-dimethoxy-benzene |
| 82 | cymoxanil | 160–161 | 2-cyano-N-ethylcarbamoyl-2-methoxyiminoacetamide |
| 83 | captan | 178 | N-trichloromethylthiotetra-hydrophthalamide |
| 84 | folpet | 177 | N-trichloromethylthio-phthalimide |
| 85 | thiophanate-methyl | 195 | dimethyl 4,4'-(o-phenylene)-bis(3-thioallophanate) |
| 86 | thiabendazole | 304–305 | 2-(thiazol-4-yl)benzimida-zole |
| 87 | chlorothalonil | 240–241 | tetrachloroisophthalo-nitrile |
| 88 | dichloran | 195 | 2,6-dichloro-4-nitroaniline |
| 89 | captafol | 160–161 | cis-N-[1,1,2,2-tetrachloro-ethyl)thio]cyclohex-4-ene-1,2- dicarbioximide |
| 90 | iprodione | 133–136 | 3-(3,5-dichlorophenyl)-N-(1-methylethyl)-2,4-dioxo-1-imidazolidine carboxamide |
| 91 | vinclozolin | 108 | 3-(3,5-dichlorophenyl)-5-ethenyl-5-methyl-2,4-oxazolidinedione |
| 92 | kasugamycin | 202–204 (DEC) | kasugamycin |
| 93 | triadimenol | 121–127 | beta-(4-chlorophenoxy)-α-(1,1-dimethylethyl)-1-H-1,2,4-triazol-1-ethanol |
| 94 | flutriafol | 130 | +-α-(2-fluorophenyl)-α-(4-fluorophenyl)-1H-1,2,4-triazole-1-ethanol |
| 95 | flusilazol | 52–53 HCl 201–203 | 1-[[bis(4-fluorophenyl)-methylsilyl)methyl]-1H-1,2,4-triazole |
| 96 | hexaconazole | 111 | (+/−)-α-butyl-α-(2,4-di chlorophenyl)-1H-1,2,4-triazole-1-ethanol |
| 97 | fenarimol | 117–119 | α-(2-chlorophenyl)-α-(4-chlorophenyl)-5-pyri-dinemethanol |
| | | BACTERICIDES | |
| 98 | oxytetracycline dihydrate | 181–182 (DEC) | oxytetracycline dihydrate |
| | | ACARICIDES | |
| 99 | hexathiazox | 108–109 | trans-5-(4-chlorophenyl)-N-cyclohoxyl-4-methyl-2-oxo-3-thiazolidinecarboxamide |
| 100 | oxythioquinox | 169–170 | 6-methyl-1,3-dithiolo-[2,3-B]quinonolin-2-one |
| 101 | dienochlor | 122–123 | bis(pentachloro-2,4-cyclo-pentadien-1-yl) |
| 102 | cyhexatin | 245 | tricyclohexyltin hydroxide |
| 103 | fenbutatin oxide | 145 | bis(tris(2-methyl-2-phenyl-propyl)tin] oxide |
| | | INSECTICIDES | |
| 104 | carbofuran | 150–152 | methylcarbamic acid, ester with 2,3-dihydro-2,2-di-methyl-7-benzofuranol |
| 105 | carbaryl | 142 | methylcarbamic acid, ester with a-naphthol |
| 106 | thiodicarb | 173–174 | dimethyl N,N'-[thiobis-(N-methylimmo)carbonyl-oxy]]-bis[ethanimido-thioate] |
| 107 | deltamethrin | 98–101 | α-cyano-3-phenoxybenzyl-cis- |

TABLE 1-continued

| Cmpd. No. | Common Name | m.p. (°C.) | Chemical Name |
|---|---|---|---|
| 108 | tetrachlorvinphos | 93–98 | 3-(2,2-dibromovinyl)-2,2-dimethylcyclopropane carboxylate (Z)-2-chloro-1-(2,4,5-tri-chlorophenyl)vinyl dimethyl phosphate |

The compositions of this invention contain at least one water-soluble diluent. This is defined as a water-soluble polymer, salt, surfactant, hydrated organic or inorganic compound or carbohydrate which melts or softens at elevated temperatures and acts as the primary extrusion aid. It has been discovered that, in some cases, a suitable water-soluble diluent may have a melting point significantly higher than the extrusion temperature but it will nevertheless function as an effective extrusion aid. Apparently it forms a lower melting eutectic mixture with other soluble ingredients in the composition. For example, urea has a sharp melting point at 133° C. which is higher than typical extrusion temperatures. Napthalene sulfonates and their condensates, which are well known in the art as dispersants and wetting agents for agricultural formulations, have no melting point. However, a mixture of the two in the presence of residual moisture in the composition, will soften at temperatures as low as 80° C. making the urea an effective extrusion aid. Some non-limiting examples of suitable water-soluble diluents are hydroxyethylcellulose, sorbitol, lactose, urea, ethylurea, polyvinyl alcohol and sodium acetate trihydrate.

In a preferred embodiment, the compositions of this invention include a heat activated binder along with the water soluble diluent. The heat-activated binder (HAB) is a solid, surface active material which dissolves rapidly in water, has some viscosity near its melting point, and is capable of acting as a binder and extrusion aid when heat is applied. At an elevated temperature the binder softens and melts, thereby becoming sticky enough to bind the pesticidal particles into larger aggregates. It is theorized that the softened or melted HAB can also function as a plastic or viscoelastic lubricant allowing the composition to extrude more easily through a die or screen. The preferred melting point range for the HAB is 45° C. to 100° C. Examples of suitable HABs, which are not intended to be limiting, are ethylene oxide/propylene oxide copolymers, polyethoxylated alkylphenols, polyethoxylated fatty acids or alcohols and polyethylene glycol. Preferred HAB's are ethylene oxide/propylene oxide copolymers and polyethoxylated alkylphenols. Most preferred are block copolymers of ethylene oxide/propylene oxide where 80% is ethylene oxide and 20% is propylene oxide, and polyethoxylated dinonyl phenol with approximately 150 moles of ethylene oxide.

The composition also contains disintegrant(s) which wick in water and physically expand to aid break-up of the granule. Non-limiting examples of suitable disintegrants include starch, cross-linked polyvinylpyrrolidone, microcrystalline cellulose, cross-linked sodium carboxymethyl cellulose, sodium starch glycolate, soy polysaccharide and ion exchange resins. Cross-linked polyvinylpyrrolidone and cross-linked sodium carboxymethyl cellulose are preferred.

Dispersant(s) are needed to help disperse the active ingredient in water. Non-limiting examples of suitable dispersants include sodium and ammonium salts of napthalene sulfonate-formaldehyde condensates; sodium, calcium and ammonium salts of ligninsulfonates (optionally polyethoxylated); sodium and ammonium salts of maleic anhydride copolymers and sodium salts of condensed phenolsulfonic acid.

Optional additives include:

(1) Anticaking agents to prevent clumping of granules when stored under hot warehouse conditions. Non-limiting examples include sodium and ammonium phosphates, sodium carbonate and bicarbonate, sodium acetate, sodium metasilicate, magnesium, zinc and calcium sulfates, magnesium hydroxide, (all optionally as hydrates), anhydrous calcium chloride, molecular sieves, sodium alkylsulfosuccinates, calcium and barium oxides.

(2) Chemical stabilizers to prevent decomposition of the active(s) during storage. Non-limiting examples of suitable chemical stabilizers include alkaline earth and transition metal sulfates such as magnesium, zinc, aluminum and iron; sodium hexametaphosphate, calcium chloride and boric anhydride.

(3) Gas producing disintegrants for faster breakup of the granule in water. Non-limiting examples of suitable gas generating additives are combinations of sodium and potassium bicarbonates and carbonates with acids such as citric and fumaric acid.

(4) Wetting agents to improve the speed of wetting upon mixing with water. Non-limiting examples of suitable anionic wetting agents include sodium salts of alkyl napthalene sulfonates, alkyl benzene sulfonates, alkyl sulfosuccinates, taurates, alkyl sulfates and phosphate esters. Examples of suitable nonionic wetting agents include acetylenic diols and alkyl phenol ethoxylates.

(5) Inert fillers, including but not limited to inorganic fillers well known in the art. Non-limiting examples are swelling and non-swelling clays, synthetic and diatomaceous silicas, calcium and magnesium silicates, titanium dioxide, aluminum, calcium and zinc oxide, calcium and magnesium carbonate, ammonium, sodium, potassium, calcium and barium sulfate, charcoal.

The granules of this invention beak up rapidly and form high quality dispersions in water as determined from the Long Tube Sedimentation test described in U.S. Pat. No. 3,920,442 col.9, lines 1 to 39. Acceptable Long Tube Sedimentation values correspond to 0.02 ml, preferably 0.01 ml of solids after 5 minutes of settling. The granules should exhibit low attrition characteristics which can be determined by the attrition test in U.S. Pat. No. 3,920,442 col 8, lines 5 to 48. The test is modified to use test samples of the appropriate granule size (e.g. 14–20 U.S. mesh). Attrition values of less than 40% and preferably less than 30% are acceptable.

The following examples are presented to illustrate, but not to restrict, this invention.

| Identity of Ingredients Used in Examples | |
|---|---|
| Name | Identity |
| Macol ® DNP150 (Mazer Chemicals) | Polyethoxylated dinonylphenol (150 moles ethylene oxide) |
| Pluronic ® F108 (BASF Corp) | 80% Ethylene oxide/20% propylene oxide block copolymer |
| Polyplasdone ® XL-10 (GAF Corp) | Crosslinked polyvinyl pyrrolidone |
| Lomar ® PWA (Henkel Corp) | Ammonium napthalene sulfonate-formaldehyde condensate |
| Morwet ® EFW (Witco Corp) | Mixture of alkyl carboxylate and Sodium alkyl napthalene sulfonate |

EXAMPLE 1

A 150 gm premix was formulated from the ingredients listed below. The ingredients were blended and then passed through a MikroPulverizer hammer mill. The milled premix was slowly added to a 1 inch Wayne single screw extruder with a 25:1 L/D ratio. The extruder had three electrical heating zones along the barrel plus a band heater for the die. Temperatures were generally kept as uniform as possible along the barrel and the die. A mechanical or electronic pressure indicator was fitted near the end of the barrel to measure hydraulic pressures close to the die.

The premix was extruded through a die containing 8×1 mm holes arranged in a circular pattern. The extruded product was allowed to cool for a few minutes then it was chopped up in a small food processor and screened to obtain the 14 to 35 U.S. sieve cut size.

Extruder temperature range 87°–91° C.
Hydraulic pressure range 0–50 psi

| Premix Formulation | |
|---|---|
| | Weight Percent |
| Diuron technical | 62.4 |
| Lomar ® PWA | 10.0 |
| Macol ® DNP150 | 5.0 |
| Morwet ® EFW | 2.0 |
| Polyplasdone ® XL-10 | 2.0 |
| Urea | 18.6 |

| Properties of Granules | |
|---|---|
| Long Tube Sedimentation | .002 |
| Long Tube Sedimentation after aging 2 weeks @ 54 C. | .002 |
| % Attrition (14–20 mesh cut) | 1.7 |
| Bulk Density (lb/cu ft) | 39.8 |

EXAMPLE 2

The procedure of Example 1 was used with the following premix. The die had 6×1 mm holes arranged in a hexagonal pattern.
Extrusion temperature range 88°–94° C.
Hydraulic pressure range 0–1000 psi

| Premix Formulation | |
|---|---|
| | Weight Percent |
| Diuron technical | 62.4 |
| Lomar ® PWA | 7.0 |
| Pluronic ® F108 | 5.0 |
| Polyplasdone ® XL-10 | 2.0 |
| Citric acid anhydrous | 2.0 |
| Sodium bicarbonate | 3.0 |
| Urea | 18.6 |

| Properties of Granules | |
|---|---|
| Long Tube Sedimentation | .002 |
| Long Tube Sedimentation after aging 2 weeks @ 54 C. | trace |
| % Attrition (14–20 mesh cut) | 8.7 |
| Bulk Density (lb/cu ft) | 25.1 |

EXAMPLE 3

The procedure of example 2 was used with the following premix.
Extrusion temperature range 88°–94° C.
Hydraulic pressure range 300–500 psi
Screw speed 26 rpm

| Premix Formulation | |
|---|---|
| | Weight Percent |
| Diuron technical | 62.4 |
| Lomar ® PWA | 7.0 |
| Macol ® DNP150 | 5.0 |
| Polyplasdone ® XL-10 | 2.0 |
| Citric acid anhydrous | 5.0 |
| Sodium carbonate anhydrous | 4.0 |
| Urea | 14.6 |

| Properties of Granules | |
|---|---|
| Long Tube Sedimentation | trace |
| Long Tube Sedimentation after aging 2 weeks @ 54 C. | .002 |
| % Attrition (14–20 mesh cut) | 8.3 |
| Bulk density (lb/cu ft) | 23.9 |

EXAMPLE 4

The procedure of example 2 was used with the following premix:
Extrusion temperature range 86°–91° C.
Hydraulic pressure range 100–300 psi
Screw speed 26 rpm

| Premix Formulation | |
|---|---|
| | Weight Percent |
| Diuron technical | 62.4 |
| Lomar ® PWA | 7.0 |
| Macol ® DNP150 | 5.0 |
| Polyplasdone ® XL-10 | 2.0 |
| Citric acid anhydrous | 5.0 |
| Sodium carbonate anhydrous | 4.0 |
| Calcium sulfate anhydrous | 3.0 |
| Urea | 11.6 |

-continued

| Premix Formulation | |
|---|---|
| | Properties of Granules |
| Long Tube Sedimentation | 0 |
| Long Tube Sedimentation after aging 2 weeks @ 54 C. | .002 |
| % Attrition (14–20 mesh cut) | 6.7 |
| Bulk density (lb/cu ft) | 24.8 |

EXAMPLE 5

The procedure of Example 2 was used with the following premix:
Extrusion temperature range 84°–92° C.
Hydraulic pressure range 100–300 psi
Screw speed 30 rpm

| Premix Formulation | |
|---|---|
| | Weight Percent |
| Methyl 2-[[[[(4-methyl-6-methoxy-1,3,5-triazin-2-yl)amino]carbonyl]amino]-sulfonyl]benzoate | 52.0 |
| Lomar ® PWA | 7.0 |
| Pluronic ® F108 | 8.0 |
| Polyplasdone ® XL-10 | 2.0 |
| Citric Acid anhydrous | 1.0 |
| Sodium bicarbonate | 1.5 |
| Sorbitol | 28.5 |
| | Properties of Granules |
| Long Tube Sedimentation | trace |
| Long Tube Sedimentation after aging 2 weeks @ 54 C. | .004 |
| % Attrition (14–20 mesh cut) | 0.7 |
| Bulk density (lb/cu ft) | 39.6 |

EXAMPLE 6

The procedure of Example 2 was used with the following premix. 200 gm of premix was prepared for extrusion.
Extrusion temperature range 84°–87° C.
Screw speed 30 rpm

| Premix Formulation | |
|---|---|
| | Weight Percent |
| Methyl 2-[[[[(4-methyl-6-methoxy-1,3,5-triazin-2-yl)amino]carbonyl]amino]-sulfonyl]benzoate | 52.0 |
| Lomar ® PWA | 7.0 |
| Pluronic ® F108 | 8.0 |
| Polyplasdone ® XL-10 | 2.0 |
| Citric acid anhydrous | 1.0 |
| Sodium bicarbonate | 1.5 |
| Type 4A molecular sieve (pulverized) | 4.0 |
| Sorbitol | 24.5 |
| | Properties of Granules |
| Long Tube Sedimentation | .002 |
| Long Tube Sedimentation | .003 |

| Premix Formulation | |
|---|---|
| after 2 weeks @ 54° C. Bulk density (lb/cu ft) | 39.0 |

What is claimed is:

1. Water-dispersible granular compositions made by extruding at elevated temperature a dry premix comprising by weight based on the total weight of the composition:
   1) 0.01–90% of one or more active ingredients which are stable at the extrusion temperature;
   2) 1–60% of one or more water-soluble diluents;
   3) an effective amount of one or more water-soluble heat activated binders that melt at temperatures between 40°–120° C.; and
   4) two or more additives selected from the group consisting of:
      a) up to 10% anti caking agent(s);
      b) up to 10% chemical stabilizer(s);
      c) up to 20% gas generators;
      d) 0.1–10% disintegrant(s);
      e) 0.1–20% dispersant(s);
      f) up to 5% wetting agent(s); and
      g) up to 80% inert filler(s);
   and the sum of all the ingredients in a composition is 100%.

2. The composition of claim 1 wherein the active ingredient(s) comprise 10–70%, and the heat activated binder(s) comprise 1–30%.

3. The composition of claim 1 wherein the active ingredient(s) comprise 10–70%, and the heat activated binder(s) comprise 1–15%.

4. The composition of claim 3 wherein the heat activated binder(s) is selected from the group consisting of polyethoxylated dinonylphenol, ethylene oxide/propylene oxide copolymer and mixtures of the foregoing.

5. The composition of claim 4 wherein the water soluble diluent is urea, ethylurea, sorbitol, lactose or sodium acetate trihydrate and mixtures thereof.

6. The composition of claim 5 wherein the ethylene oxide/propylene oxide copolymer if present is about 80% ethylene oxide and 20% propylene oxide and the polyethoxylated dinonylphenol has 150 ethylene oxide units.

7. The composition of claim 5 wherein the water soluble diluent is urea or sorbitol.

8. The composition of claim 7 wherein the active ingredient is selected from the group consisting of methyl 2-[[[[(4,6-dimethyl-2-pyrimidinyl)amino]carbonyl]amino]sulfonyl]benzoate;

methyl 3-[[[[(4-methoxy-6-methyl-1,3,5-triazin-2-yl)amino]carbonyl]amino] sulfonyl] -2-thiophenecarboxylate;

2-chloro-N-[[(4-methoxy-6-methyl-1,3,5-triazin-2-yl)amino]carbonyl]-benzene-sulfonamide;

ethyl 2-[[[[(4-chloro-6-methoxy-2-pyrimidinyl)amino] carbonyl]amino] sulfonyl]benzoate;

methyl 2-[[[[(4-methyl-6-methoxy-1,3,5-triazin-2-yl)amino]carbonyl]amino] sulfonyl] benzoate;

2-[[[[(4,6-dimethoxy-2-pyrimidinyl)amino] carbonyl] amino]sulfonyl]-N, N-dimethyl- 3-pyridinecarboxamide;

methyl 2-[[[[4-ethoxy-6-(methylamino- 1,3,5-triazin-2-yl]amino]carbonyl] amino]sulfonyl]benzoate;

methyl 2-[[[[N-(4-methoxy-6-methyl-1,3,5 -triazin-2-yl)-

N-methylamino]carbonyl] amino]sulfonyl]benzoate;

methyl 2-[[[[[(4,6-dimethoxy-2-pyrimidinyl)amino]carbonyl]amino]sulfonyl] methyl]benzoate;

N-[[(4,6-dimethoxy-2-pyrimidinyl)amino] carbonyl]-3-(ethylsulfonyl)-2-pyridine sulfonamide;

methyl 2-[[[[[4,6-bis(difluoromethoxy)-2-pyrimidinyl] amino]carbonyl] amino]sulfonyl]benzoate;

2-(2-chloroethoxy)-N-[(4-methoxy-6-methyl-1,3,5-triazin-2-yl)aminocarbonyl] benzene sulfonamide;

ethyl 5-[[[(4,6-dimethoxy-2-pyrimidinyl)amino]carbonyl]amino]sulfonyl] -1-methyl-1H-pyrazole-4-carboxylate; and N-[[(4,6-dimethoxy-2-pyrimidinyl) amino] carbonyl]-1-methyl-4-(2-methyl-2H-tetrazol- 5-yl)-1H-pyrazole-5-sulfonamide.

9. A process comprising extruding a dry premix of the composition of any one of claims 1–7 through a die or screen at a temperature from 50° C. to 130° C. to form granules.

10. The composition of claim 1 wherein the water-soluble diluent(s) is selected from the group consisting of hydroxyethylcellulose, sorbitol, lactose, urea, ethylurea, polyvinyl alcohol and sodium acetate trihydrate.

* * * * *